United States Patent [19]

Xu

[11] Patent Number: 5,316,909
[45] Date of Patent: May 31, 1994

[54] METHOD FOR INCREASING FLUORESCENCE

[75] Inventor: Yongyuan Xu, Beijing, China

[73] Assignee: Wallac Oy, Finland

[21] Appl. No.: 851,561

[22] Filed: Mar. 13, 1992

[30] Foreign Application Priority Data

Mar. 15, 1991 [FI] Finland ............................... 911297

[51] Int. Cl.$^5$ .......................................... G01N 33/545
[52] U.S. Cl. ...................................... 435/6; 436/501;
  436/531; 436/537; 436/538; 436/546; 436/827
[58] Field of Search ............... 436/827, 501, 537, 546,
  436/547, 538, 531; 435/6

[56] References Cited

U.S. PATENT DOCUMENTS

| | | | |
|---|---|---|---|
| 4,058,732 | 11/1977 | Wieder . | |
| 4,374,120 | 2/1983 | Soini et al. | 436/536 |
| 4,808,541 | 2/1989 | Mikola et al. | 436/501 |
| 4,857,475 | 8/1989 | Dakubu | 436/546 |
| 5,124,268 | 6/1992 | Dakubu | 436/537 |

FOREIGN PATENT DOCUMENTS 8707955 12/1987 World Int. Prop. O. .

OTHER PUBLICATIONS

Soini, E., Hemmilä, I., Clin.Chem. 1979, 25, 353–361.
Yang Jinghe et al., (1987) Anal. Chim. Acta, 198, 287.
Ci Yunxiang et al., (1988) Analyst (London) 113, 1453.
Ci. Yunxiang et al., (1989) Analyst (London) 114, 1417.
Ci, Yun–Xiang et al., Analytical Letters, 21(8), 1499–1513 (1988).
Xu et al., Medline Abstract 92117276 (1991), "Co--fluorescence of europium and samarium in time-resolved fluorimetric immunoassays".
Hemmila et al., Analytical Biochemistry, vol. 137, 335–343 (1984).
Yang et al., Chem. Abstracts, vol. 114 (1991), abstract No. 114206z.
Yang et al., Chem. Abstracts, vol. 113 (1990), abstract No. 125561s.

Primary Examiner—Mary E. Ceperley
Attorney, Agent, or Firm—Pollock, Vande Sande & Priddy

[57] ABSTRACT

The invention relates to a method based on fluorescence, especially time-resolved fluorescence for quantitative assay of a bioaffinity reaction involving bioaffinity components. The method comprises the labelling of one or several of the bioaffinity components participating in the reaction with a lanthanide chelate, forming of a lanthanide chelate for a fluorescence measurement after the reaction, and measuring the fluorescence of the chelate. The lanthanide (Eu, Tb, Sm or Dy) is brought to a strongly fluorescent form before the fluorescence measurement by incorporating the lanthanide in an aggregated particle that comprises the lanthanide chelate and a chelate of a fluorescence-increasing ion (Y, Gd, Tb, Lu or La) to bring about a cofluorescence effect. An aliphatic or aromatic beta-diketone is used as the chelating compound in the aggregate.

15 Claims, 3 Drawing Sheets

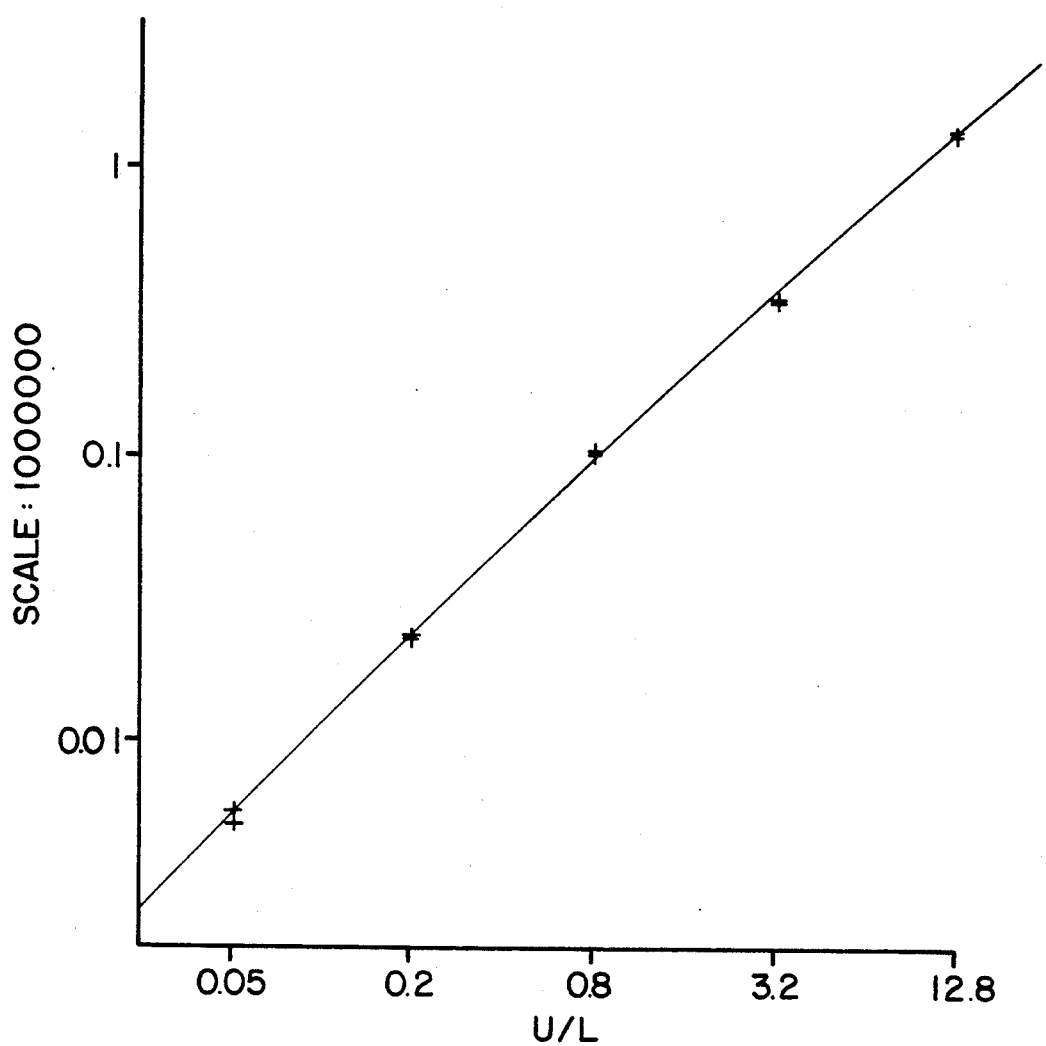
F I G. 3

METHOD FOR INCREASING FLUORESCENCE

BACKGROUND OF THE INVENTION

In the specific assay methods based on bioaffinity the analytes are usually measured at very small concentrations, which require the use of labelling agents that are detectable by a very sensitive method. Such bioaffinity assays include inter alia immunochemical assays, nucleic acid hybridizations, lectin reactions as well as receptor assays. Various labelling agent methods are usually used in the analytical applications of all these reactions. The radioisotopes are conventional labelling agents used for example in radio immunological (RIA) and immonoradiometric (IRMA) assays, which are the most sensitive specific analytical methods used in the practice. The detection sensitivity of the RIA assays is ca. $10^{-14}$M and the corresponding sensitivity limit of the IRMA assays is ca. $10^{-16}$M. Despite the common usage, the radioisotopes as labelling agents present some drawbacks such as a limited lifetime as well as handling problems. For this reason, active research has been directed to possibilities to replace the radio active labelling agents with other alternatives.

The fluorescence methods are more and more widely used in chemical, biochemical and medicinal analytics. Fluoroimmunological and immunofluorometric assays that are based on time-resolved fluorometrics and on lanthanide chelates as labelling agents give at least the same or even better sensitivity compared with RIA and IRMA assays.

Fluorescent Labelling Agents

The sensitivity of fluorescent labelling agents is high in theory for example in immunoassays, but in the practice the background of the fluorescence forms a factor limiting the sensitivity. Background fluorescence is emitted both by the components contained in the sample and by the appliances and instruments used in the measurement. In some cases where a very high sensitivity is not needed the use of fluorescent labelling agents has been possible, but the intensity of the background fluorescence often imposes real problems. For example various components contained in the serum cause often a problem of this type. The scattering caused by the sample causes also some interference especially when labelling agents with a small Stoke's shift ($<50$ nm) are used. Because of a high background and scattering the sensitivity of the labelling agents is about 50 to 100 times lower compared with the sensitivity of the same labelling agent in a pure buffered solution.

Time-Resolved Fluorometry and Lanthanide Fluorescence

The time-resolved fluorescence (vide Soini, E., Hemmilä, I., Clin. Chem. 1979, 25, 353-361) gives a possibility to separate the specific fluorescence of the labelling agent from the interfering non-specific fluorescence of the background. The use of the time-resolved fluorescence for assays based on bioaffinity reactions are described in U.S. Pat. Nos. 4,058,732 and 4,374,120. In the time-resolved fluorescence the fluorescing labelling agent is excited by a short-time light pulse and the fluorescence is measured after a certain time from the moment of excitation. During the interval between the excitation moment and measurement moment the fluorescence of the interfering components becomes extinguished to such an extent that only the fluorescence emanating from the labelling agent will be measured. A labelling agent of this type should have a high fluorescence intensity, relatively long wavelength of emission, large Stoke's shift, sufficiently long half-life of fluorescence and further, the labelling agent should be capable of binding covalently to an antibody or antigen in such a way that it has no effect on the properties of these immunocomponents.

Some lanthanide chelates such as certain europium, samarium and terbium chelates have a long half-life of fluorescence and hence they are very suitable labelling agents for time-resolved fluorometry. The emission wavelength is relatively long (terbium 544 nm, europium 613 nm, samarium 643 nm) and the Stoke's shift is very large (230 to 300 nm). The most important property is, however, the long half-time of fluorescence, ca. 50-100 $\mu$s, which makes the use of time-resolved techniques possible. The fluorescence of the labelling agent can be measured when the labelling agent is bound to an antigen or antibody, or the lanthanide can be separated from them in properly chosen circumstances by dissociating the bond between the lanthanide and the chelate. After the dissociation the fluorescence of the lanthanide is measured in a solution in the presence of a beta-diketone, synergistic compound and detergent that together with the lanthanide form a micellar structure together with the lanthanide where the fluorescence intensity of the lanthanide is very high (U.S. Pat. No. 4,545,790). A solution that contains beta-diketone, a synergistic compound and detergent at a low pH-value is called a fluorescence developer solution.

In year 1967 it was proved that the fluorescence of a europium- (or samarium)-TTA-collidine complex is enhanced very strongly when $Gd^{3+}$ or $Tb^{3+}$ is added (Melanteva et al. (1967), Zh. Anal Khim. 22, 187). The phenomenon was not, however, studied in more detail. During the last few years in course of studies of europium and samarium chelates in the presence of TTA and a synergistic ligand it has been found out that the strong enhancement of the fluorescence is based on internal fluorescence effect that is called cofluorescence. Several studies have been published on the subject recently (Yang Jinghe et al. (1987) Anal. Chim. Acta, 198, 287; Ci Yunxiang et al. (1988), Analyst (London), 113, 1453; Ci Yunxiang et al. (1988), Anal. Lett., 21, 1499; Ci Yunxiang et al. (1989), Anal. Chem., 61, 1063; Yang Jinghe (1989), Analyst (London), 114, 1417). All studies up to present have employed only one beta-diketone (TTA), two fluorescent lanthanides ($Eu^{3+}$ and $Sm^{3+}$) and the determinations have been carried out in the presence of lanthanide and yttrium ions for determining trace amounts of Eu and Sm in lanthanide and yttrium oxides.

SUMMARY OF THE INVENTION

The present invention is based on a method which increases the fluorescence of lanthanide chelates when they are used as labelling agents for fluorometric assay of biologically active substances. The lanthanide is converted to a highly fluorescent form before the measurement based on a time-resolved fluorescence by forming aggregated particles that contain a lanthanide chelate as well as a chelate that contains an ion increasing the fluorescence. The specific fluorescence of lanthanides in the above-mentioned fluorescent aggregates is considerably increased. The fluorescence intensity of the lanthanide chelate is thereby enhanced when biologically active substances are measured. Europium, terbium, samarium or dysprosium are used as the lanthanides of the lanthanide chelates.

BRIEF DESCRIPTION OF THE DRAWINGS

In the appended drawings,

FIG. 3 shows the results of an immunoassay by the method of the invention.

DETAILED DESCRIPTION OF THE INVENTION

Figure 1:
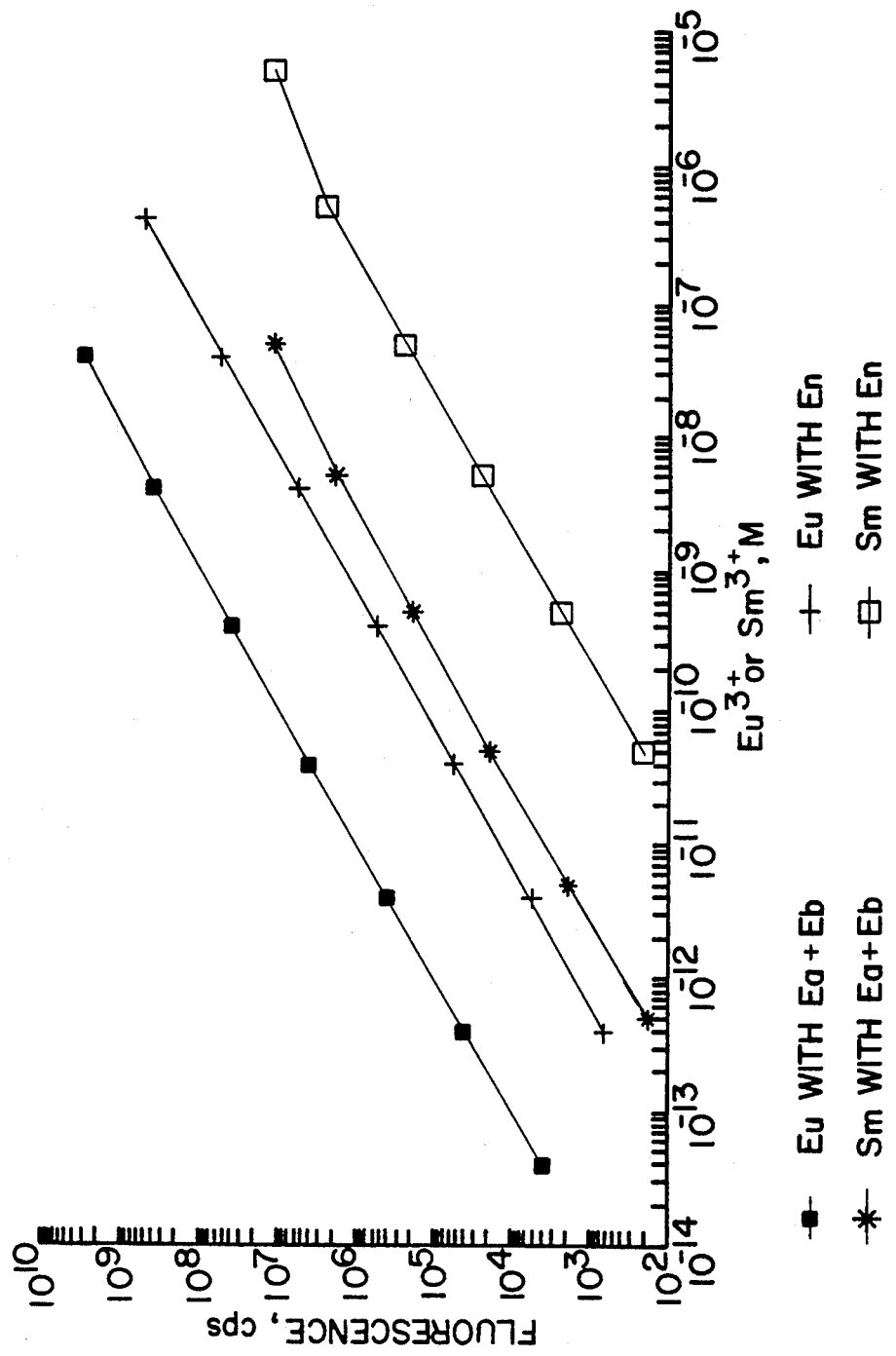
FIG. 1 shows standard curves of Eu and Sm obtained with the solutions used in the method.

The present invention has proved the fact that the beta-diketones presented in table I give a good cofluorescence effect. The aromatic beta-diketones shown in table I are well applicable to the measurement of europium and samarium in a cofluorescence method, whereas the aliphatic beta-diketones of the table are applicable to the measurement of europium, terbium, samarium and dysprosium by another method based on the cofluorescence. The invention proves the fact that the fluorescence intensity of europium and samarium, and in addition terbium and dysprosium, is greatly enhanced when other lanthanides and yttrium are used in the cofluorescence. It should be mentioned that terbium, which has an unusual cofluorescence effect, can be used as a fluorescence -enhancing ion when the cofluorescence of europium and samarium is to be enhanced when an aromatic beta-diketone is used. It can be also used as a fluorescent ion whose fluorescence is enhanced by another lanthanide ion or yttrium ion when an aliphatic beta-diketone is used in the cofluorescence.

The beta-diketones of table 1 form the chelates both with the fluorescent lanthanide ion and with the ion enhancing the fluorescence, when used in accordance with the invention.

For increasing the fluorescence further, synergistic compounds must be used in the cofluorescence method. Such compounds are 1,10-phenanthroline (Phen)
4,7-dimethyl-1,10-phenanthroline (4,7-DMphen),
4,7-diphenyl-1,10-phenanthroline (4,7-DPphen),
5,6-dimethyl-1,10-phenanthroline (5,6-DMphen),
2,9-dimethyl-4,7-diphenyl-1,10-phenanthroline (DMDPphen),
2,2$^1$-dipyridyl (DP),
2,2$^1$-dipyridylamine (DPA),
2,4,6-trimethylpyridine (TMP),
2,2$^1$:6$^1$,2$^{11}$-terpyridine (TP),
1,3-diphenylguanidine (DPG).

The synergistic compounds form a structure completing the chelate structure of the lanthanide chelates and they are at the same time hydrophobic, thus inhibiting the action of water tending to quench fluorescence.

The strong fluorescence of the lanthanide chelates is based on the fact that the ligand absorbs the excitation energy, whereafter the energy is transferred from the triplet level of the ligand to the resonance level of the lanthanide. The consequence is a very sharp emission peak whose wavelength is characteristic of the lanthanide ion. In addition, the emission has a long half-life. The cofluorescence is based on an intermolecular energy transfer that occurs from the chelate of the ion increasing fluorescence, the energy donor, to the chelate of the fluorescent ion, the energy acceptor, provided that the cofluorescence complex is in the solution as a suspension or in solid form as aggregated particles and that the solution contains a large excess of the chelate containing the ion increasing the fluorescence. In aggregated particles the chelate containing the fluorescent lanthanide ion is in a close contact with several lanthanide chelate complexes increasing fluorescence so that the energy can effectively be transferred from the latter to the former.

Ions increasing the fluorescence that are suitable for cofluorescence are $Gd^{3+}$, $Tb^{3+}$, $Lu^{3+}$, $La^{3+}$ and $Y^{3+}$. The ion must always be used in a large excess so that the ion increasing the fluorescence influences the fluorescent ion ($Eu^{3+}$, $Tb^{3+}$, $Sm^{3+}$ or $Dy^{3+}$) to increase its intensity 10 to 1000 fold. In some cases fluorescence was not at all detected without a cofluorescence complex increasing the fluorescence, but the presence of said complex caused a strong fluorescence by the fluorescent ion.

In most of the cofluoresence complexes the presence of a detergent, such as TRITON X-100, TRITON X-100, TRITON N-101 and TRITON X-405 has an effect on the fluorescence intensity and its stability. The micelles formed protect the fluorescent chelates from the quenching action by the water and at the same time keep the cofluorescence complex in suspension.

Water-soluble organic solvents such as ethanol, propanol, dimethylsulfoxide, 2-metoxyethanol or ethyleneglycol increase often the fluorescence of the fluorescent ion in the cofluorescent complex.

The determination based on cofluorescence can be used in various ways when assaying biological substances. The biological substance can be labelled with the lanthanide chelate using a chelating compound such as some EDTA analogue. After the immunochemical assay the lanthanide ion is dissociated from the labelled biological substance into a solution, whereafter the very strongly fluorescent aggregated particle is formed (cofluorescent complex), consisting of the lanthanide chelate and the chelate of the ion increasing fluorescence. The biological substance can also be labelled directly with very strongly fluorescent particles by using a chemical bond or adsorption. After the immunochemical reaction the fluorescence of the particles is measured either in suspension in a solution or directly on the surface of a solid support. Alternatively, the biological substance can be labelled only with a beta-diketone derivative or with a synergistic compound that have a group that enables their coupling to an immunocomponent such as to a protein. After the immunochemical assay, a strongly fluorescent aggregated particle is created that contains the lanthanide chelate as well as the excess of the chelate of the ion increasing fluorescence. In this case, also an excess of the chelate of the fluorescent ion is used, whereby a lanthanide contamination will not interfere, and the fluorescence can be measured directly from the surface of a solid support, if desired. Homogeneous assays excluding the separation stage can utilize factors that influence the cofluorescence by increasing or quenching the intensity, for example. Such factors are for example antigen-antibody reactions and compounds affecting the energy transfer. The assay based on cofluorescence can be commonly used in methods based on bioaffinity reactions, such as immunochemical assays, nucleic acid hybridization assays, receptor assays as well as lectine reactions, which all use lanthanide chelates or components forming cofluorescence complexes as the labelling agents.

Because the lanthanide determinations based on the cofluorescence complex are very sensitive, these complexes can be used for a simultaneous determination of several lanthanides. Hence, several analytes can be determined in one single sample incubation in the analytical applications.

The developer solution used in the cofluorescence is usually made before the use. It consists of two different solutions, Ea and Eb, which are kept separately. When it is necessary to dissociate the lanthanide ion from the labelled biological substance, Ea contains A) the beta-diketone that chelates the fluorescent ion and the fluorescence-increasing ion, said beta-diketone being in excess compared with the ions to be chelated, B) the fluorescence-increasing ion, and C) the detergent, all in an aqueous solution whose pH is adjusted to a value below 4 with acetic or hydrochloric acid, whereas Eb contains D) the synergistic compound and E) a buffer with a pH above 6. When using the developer solutions, first the solution Ea is added, whereafter shaking is applied during 1–5 minutes to dissociate the lanthanide ion. Thereafter Eb is added and the shaking is continued for 1 to 15 minutes. During the second shaking stage a suspension containing the aggregated, very fluorescent particles is formed. The fluorescence is measured using time-resolved fluorometry.

The invention is illustrated by means of the following examples:

EXAMPLE 1

Cofluorescence developer solution for the determination of $Eu^{3+}$ and $Sm^{3+}$, containing TTA, phenanthroline, $Y^{3+}$ and TRITON X-100 surfactant.

The developer solution consists of two parts, Ea, that contains 60 $\mu M$ TTA, 7,5 $\mu M$ $Y^{3+}$, 0.06% (w/v) TRITON X-100 surfactant in an aqueous solution with a pH adjusted to 3.2 by means of acetic acid, as well as Eb, which contains 1.15 mm phenanthroline in 0.21M Tri-buffer. The developer solutions Ea and Eb were used in the ratio 10:1. FIG. 1 shows the standard curves for $Eu^{3+}$ and $Sm^{3+}$ when cofluorescence has been applied. Commercial developer solution DELFIA ® has been used as the reference (En). A clearly better result is obtained with cofluorescence compared with the DELFIA ® method.

EXAMPLE 2

Developer solution based on cofluorescence for determination of $Eu^{3+}$ and $Sm^{3+}$, containing BTA, phenanthroline, $Y^{3+}$ and TRITON X-100 surfactant.

The developer solution consists of two parts, solution Ea, which contains 50 $\mu M$ BTA, 7.5 $\mu M$ $Y^{3+}$ and 0.02% (w/v) TRITON X-100 surfactant in an aqueous solution with a pH adjusted to 3.2 by means of acetic acid, as well as solution Eb, which contains 500 $\mu M$ phenanthroline in 0.2M Tris-buffer. The solutions Ea and Eb are used in the ratio 10:1. The fluorescence results obtained with the developer solution are presented in table II.

EXAMPLE 3

Developer solution based on cofluorescence for simultaneous determination of $Eu^{3+}$, $Tb^{3+}$, $Sm^{3+}$ and $Dy^{3+}$ in a solution that contains PTA, $Y^{3+}$, TRITON X-100 surfactant and ethanol.

The developer solution consists of two parts, Ea, which contains 50 $\mu M$ PTA, 7.5 $\mu M$ $Y^{3+}$, 0.06% (w/v) TRITON X-100 surfactant and 25% (v/v) ethanol in an aqueous solution with a pH adjusted to 3.45 by means of acetic acid, and Eb, which contains 500 $\mu M$ phenanthroline in 0.2M Tris-buffer. The solutions Ea and Eb are used in the ratio 10:1. The fluorescence results obtainable with the developer solution are presented in table III.

EXAMPLE 4

A developer solution based on cofluorescence for simultaneous determination of $Eu^{3+}$, $Tb^{3+}$, $Sm^{3+}$ and $Dy^{3+}$ in a solution containing PTA, DP, $Y^{3+}$ and TRITON X-100 surfactant.

The developer solution consists of two parts, solution Ea which contains 100 $\mu M$ PTA, 3 $\mu M$ $Y^{3+}$ and 0.0006% (w/v) TRITON X-100 surfactant in an aqueous solution with a pH adjusted to 3.0 by means of acetic acid, and solution Eb, which contains 5 mM DP and 80% (v/v) ethanol in 0.375M Tris-buffer. The solutions Ea and Eb are used in the ratio of 10:1. The fluorescence results obtainable with the developer solution are presented in table IV.

EXAMPLE 5

The determination of FSH by an immunofluorometric method based on time-resolved fluorescence using the cofluorescence development (solutions Ea and Eb of Example 1).

A monoclonal anti-alfa-FSH antibody was labelled using $N^1$-(p-isothiocyanatebenzyl)-diethylenetriamine-$N^1,N^2,N^3,N^4$-tetra-acetic acid as the labelling agent. The labelling was carried out at pH 9.5 by using a 50 fold molaric excess of the Eu-chelate. The free labelling agent was separated from the labelled antibody by gel filtration (Sepharose 6B+Sephadex G 50). The labelling ratio was 17 $Eu^{3+}$/IgG. The wells of microtiter plates were coated with a monoclonal anti-beta-FSH antibody. The coating was carried out in 0.1M $NaH_2PO_4$ buffer, pH 4.5, overnight at room temperature, using 1 $\mu g$ antibody per well. The wells were washed and saturated with 0.1% BSA and stored wet at +4° C.

The immunoassay was carried out in 0.05M Tris-HCl buffer, pH 7.7, which contained 9 g/l NaCl, 0.05% $NaN_3$, 0.5% BSA, 0.05% bovine globulin and 0.01% Tween 40. The first incubation (1 hour at room temperature) was carried out in different FSH contents and the second incubation (1 hour at room temperature) was carried out by using 5 ng per well of the anti-alfa-FSH antibody labelled with Eu-chelate, whereafter the wells were washed six times.

Figure 2:
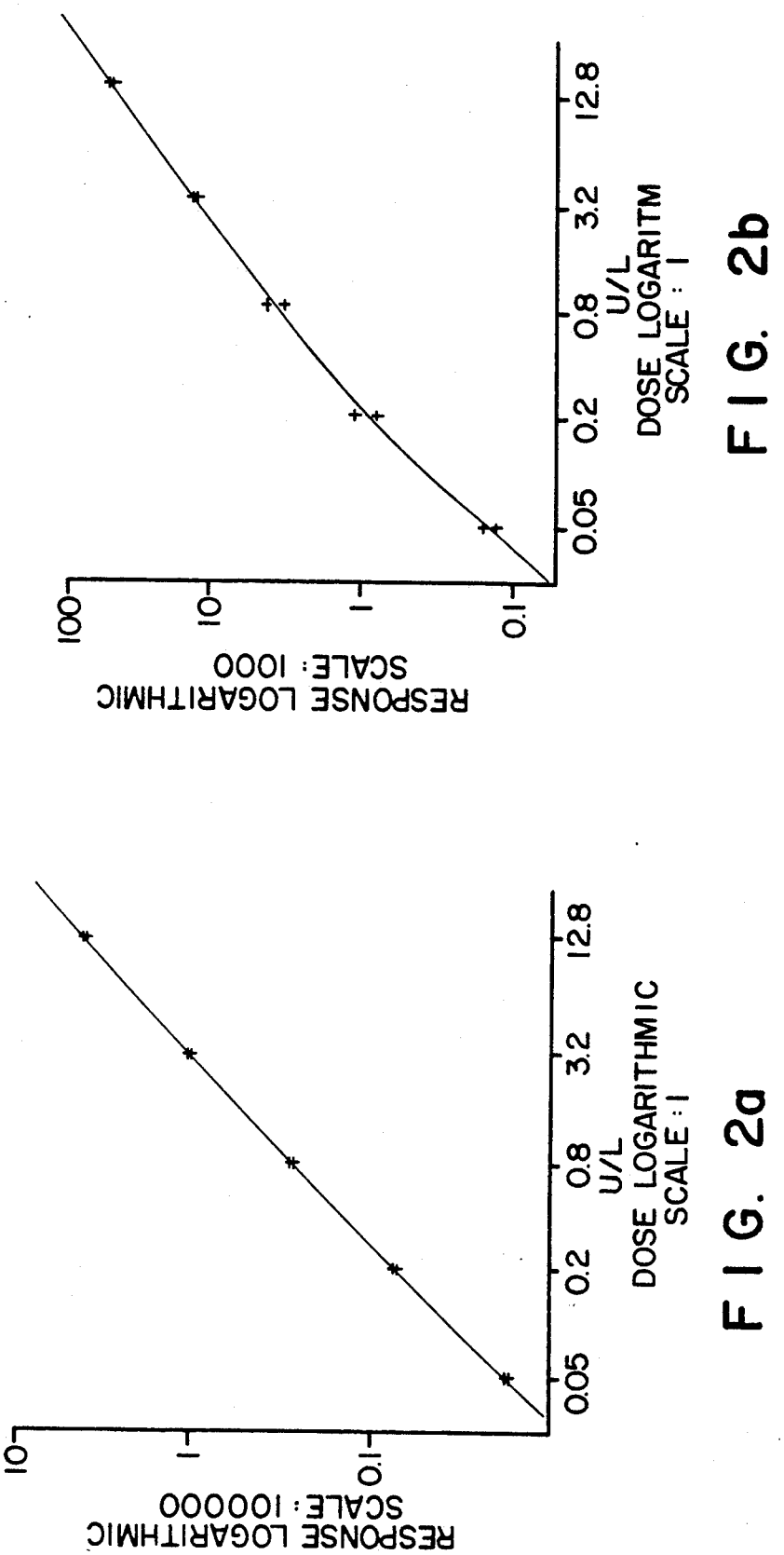
FIGS. 2a and 2b show the results of an immunoassay by the method of the invention and a commercial immunoassay method, respectively.

After the washing the europium ion was dissociated by adding 200 $\mu l$ of solution Ea per well, whereafter shaking was applied during 1 to 2 minutes. The fluorescence of the used labelling agent ($Eu^{3+}$) was developed by increasing 20 $\mu l$ of solution Eb per well, whereafter shaking was applied for 8 to 10 minutes. The fluorescence was measured by using a time-resolved fluorometer with a cycle length of 2 ms, delay between the excitation and the measurement of 0.5 ms and the measurement time of 1.5 ms. The results are presented in FIG. 2a. FIG. 2b shows the results of the same immunoassay when a commercial DELFIA ® developer solution has been used for the measurement. By using the cofluorescence, a much better result is obtained at low FSH-concentrations compared with DELFIA ®.

EXAMPLE 6

The determination of FSH by an immunofluorometric method based on time-resolved fluorescence using the solutions Ea and Eb of Example 2 in the development of cofluorescence.

The components and methods used in the immunoassay were the same as in Example 5. The dissociation of $Eu^{3+}$ and the development of fluorescence after the immunoassay took place in the following manner. The dissociation was carried out by adding 200 μl of solution Ea per well, whereafter shaking was applied for 1 to 2 minutes. The fluorescence of the labelling agent ($Eu^{3+}$) was developed by adding 20 μl of solution Eb per well, whereafter shaking was applied for 1 minute. The fluorescence was measured as in Example 5. The standard curve of the determination is presented in FIG. 3.

TABLE 1

| Beta-diketone $R_1$—CO—$CH_2$—CO—$R_2$ | $R_1$ | $R_2$ |
|---|---|---|
| Thenoyltrifluoroacetone (TTA) | (2-thienyl) | $-CF_3$ |
| Pivaloyltrifluoroacetone (PTA) | $(CH_3)_3C-$ | $-CF_3$ |
| 1,1,1-trifluoro-6methyl-2,4-heptanedione (TFMH) | $(CH_3)_2CHCH_2-$ | $-CF_3$ |
| Dipivaloylmethane (DPM) | $(CH_3)C-$ | $-C(CH_3)_3$ |
| Benzoyltrifluoroacetone (BTA) | $C_6H_5-$ | $-CF_3$ |
| 1,1,1,2,2,-pentafluoro-5-phenyl-3,5-pentanedione (PFPP) | $C_6H_5-$ | $-CF_2CF_3$ |
| 2-furoyltrifluoroacetone (FTA) | (2-furyl) | $-CF_3$ |
| p-fluorobenzoyltrifluoroacetone (FBTA) | F—(phenyl)— | $-CF_3$ |
| 1,1,1,2,2-pentafluoro-6,6-dimethyl-3,5-heptanedione (PFDMH) | $(CH_3)_3C-$ | $-CF_2CF_3$ |
| 1,1,1,2,2,3,3-heptafluoro-7,7-dimethyl-4,6-octanedione (HFDMO) | $CF_2CF_2CF_3-$ | $(CF_3)_3C-$ |
| 1,1,1,5,5,5-hexafluoroacethylacetone (HFAcA) | $F_3C-$ | $-CF_3$ |
| 1,1,1,2,2,-pentafluoro-3,5-hexanedione (PFH) | $CH_3-$ | $-CF_2CF_3$ |
| p-isothiocyanatebenzoyltrifluoroacetone (ICBTF) | S=C=N—$CH_2$—(phenyl)— | $-CF_3$ |
| Di-p-fluorobenzoylmethane ($D_pFBM$) | F—(phenyl)— | —(phenyl)—F |
| Dibenzoylmethane (DBM) | $C_6H_5-$ | $-C_6H_5$ |

TABLE II

| Fluorescent ion | Excitation (max) nm | Emission (max) nm | Delay us | Enchancement factor* | Fluorescence of 1 nM of the ion counts/s | Background counts/s | Sensitivity pM |
|---|---|---|---|---|---|---|---|
| $Eu^{3+}$ | 333 | 612 | 764 | 208 | 4194 × $10^4$ | 1860 | 0.0043 |
| $Sm^{3+}$ | 337 | 647 | 79 | 358 | 231 × $10^3$ | 204 | 0.11 |

*Fluorescence enchancement factor calculated on the measurement readings with and without the presence of $Y^{3+}$

TABLE III

| Fluorescent ion | Excitation (max) nm | Emission (max) nm | Delay us | Enchancement factor* | Fluorescence of 1 nM of the ion counts/s | Background counts/s | Sensitivity pM |
|---|---|---|---|---|---|---|---|
| $Eu^{3+}$ | 315 | 612 | 820 | 130 | 2.740.000 | 580 | 0.035 |
| $Tb^{3+}$ | 312 | 544 | 323 | 1078 | 956.000 | 2770 | 0.34 |
| $Sm^{3+}$ | 315 | 647 | 88 | 61 | 5.330 | 370 | 7.9 |

TABLE III-continued

| Fluorescent ion | Excitation (max) nm | Emission (max) nm | Delay us | Enchancement factor* | Fluorescence of 1 nM of the ion counts/s | Background counts/s | Sensitivity pM |
|---|---|---|---|---|---|---|---|
| $Dy^{3+}$ | 316 | 574 | 27 | 102 | 16.400 | 6980 | 46 |

TABLE IV

| Fluorescent ion | Excitation (max) nm | Emission (max) nm | Delay us | Enchancement factor* | Fluorescence of 1 nM of the ion counts/s | Background counts/s | Sensitivity pM |
|---|---|---|---|---|---|---|---|
| $Eu^{3+}$ | 312 | 612 | 948 | >1000 | 6.846.000 | 1000 | 0.019 |
| $Tb^{3+}$ | 312 | 545 | 239 | >1000 | 2.983.000 | 2400 | 0.27 |
| $Sm^{3+}$ | 312 | 647 | 48 | 309 | 11.200 | 100 | 3.8 |
| $Dy^{3+}$ | 312 | 575 | 11 | 985 | 24.500 | 6720 | 100 |

I claim:

1. Method based on fluorescence for quantitative assay of a bioaffinity reaction, wherein said method comprises the labelling of at least one bioaffinity component participating in a bioaffinity reaction with a lanthanide chelate, dissociating the lanthanide chelate from said component for a fluorescence measurement after the reaction, and measuring the fluorescence of the lanthanide chelate, said lanthanide being brought to a strongly fluorescent form before the fluorescence measurement by incorporating the lanthanide in an aggregated particle that comprises the lanthanide chelate and a chelate of a fluorescence-increasing ion to bring about a cofluorescence effect, said aggregates bringing about the cofluorescence effect containing the lanthanide chelate to be determined, the chelate of the fluorescence-increasing ion, free beta-diketone and a synergistic compound and being formed by applying after the reaction and dissociation successively two developer solutions, whereof the first one contains the beta-diketone in excess compared with the ions to be chelated with it and the fluorescence-increasing ion in an aqueous solution having pH below 4, and the second one contains the synergistic compound in a buffer having pH above 6.

2. Method as claimed in claim 1, wherein the lanthanide ion is selected from the group consisting of $Eu^{3+}$, $Tb^{3+}$, $Sm^{3+}$ and $Dy^{3+}$.

3. Method as claimed in claim 1, wherein the fluorescence-increasing ion is a trivalent ion selected from the group consisting of $Y^{3+}$, $Gb^{3+}$, $Tb^{3+}$, $Lu^{3+}$ and $La^{3+}$.

4. Method as claimed in claim 1, wherein the fluorescence having the cofluorescence effect is measured on a solid support.

5. Method as claimed in claim 1, wherein the fluorescence having the cofluorescence effect is measured in a solution.

6. Method as claimed in claim 1, wherein the beta-diketone is selected from the group consisting of thenoyltrifluoroacetone, pivaloyltrifluoroacetone, 1,1,1-trifluoro-6-methyl-2,4-heptanedione, dipivaloylmethane, benzoyltrifluoroacetone, 1,1,1,2,2-pentafluoro-5-phenyl-3,5-pentanedione, 2-furoyltrifluoroacetone, p-fluorobenzoyltrifluoroacetone, 1,1,1,2,2-pentafluoro-6,6-dimethyl-3,5-heptanedione, 1,1,1,2,2,3,3-heptafluoro-7,7-dimethyl-4,6-octanedione, 1,1,1,5,5,5-hexafluoroacetylacetone, 1,1,1,2,2-pentafluoro-3,5-hexanedione, p-isothiocyanatebenzoyl-trifluoroacetone, di-p-fluorobenzoylmethane and dibenzoylmethane.

7. Method as claimed in claim 1, wherein the synergistic compound is selected from the group consisting of
1,10-phenanthroline,
4,7-dimethyl-1,10-phenanthroline,
5,6-dimethyl-1,10-phenanthroline,
2,9-dimethyl-4,7-diphenyl-1,10-phenanthroline,
$2,2^1$-dipyridyl, $2,2^1$-dipyridylamine,
2,4,6-trimethylpyridine,
$2,2^1:6^1,2^{11}$-terpyridine and 1,3-diphenylguanidine.

8. Method as claimed in claim 1, wherein the aggregates contain a detergent.

9. Method as claimed in claim 8, wherein the detergent is selected from the group consisting of TRITON X-10, TRITON N-101 and TRITON X-405.

10. Method as claimed in claim 1, wherein the aggregates contain a water-soluble organic solvent.

11. Method as claimed in claim 10, wherein the water-soluble organic solvent is selected from the group consisting of ethanol, propanol, dimethylsulfoxide, 2-methoxyethanol and ethyleneglycol.

12. Method as claimed in claim 1, wherein the bioaffinity reaction is selected from the group consisting of immunoassay, nucleic acid hybridization, receptor assay and lectin reaction.

13. Method as claimed in claim 1, wherein said method is a time-resolved fluorescence method.

14. Method as claimed in claim 6, wherein the synergistic compound is selected from the group consisting of
1,10-phenanthroline,
4,7-dimethyl-1,10-phenanthroline,
5,6-dimethyl-1,10-phenanthroline,
2,9-dimethyl-4,7-diphenyl-1,10-phenanthroline,
$2,2^1$-dipyridyl, $2,2^1$-dipyridylamine,
2,4,6-trimethylpyridine,
$2,2^1:6^1,2^{11}$-terpyridine and 1,3-diphenylguanidine.

15. Method as claimed in claim 14, wherein the lanthanide ion is selected from the group consisting of $Eu^{3+}$, $Tb^{3+}$, $Sm^{3+}$ and $Dy^{3+}$; and wherein the fluorescence-increasing ion is a trivalent ion selected from the group consisting of $Y^{3+}$, $Gb^{3+}$, $Tb^{3+}$, $Lu^{3+}$ and $La^{3+}$.

* * * * *